United States Patent
Cook

(10) Patent No.: US 6,514,222 B2
(45) Date of Patent: Feb. 4, 2003

(54) POST SURGICAL APPENDAGE PROTECTOR

(76) Inventor: James Frederick Cook, 1302 Carolina Ave., Longmont, CO (US) 80501

(*) Notice: Subject to any disclaimer, the term of this patent is extended or adjusted under 35 U.S.C. 154(b) by 0 days.

(21) Appl. No.: 09/812,638

(22) Filed: Mar. 20, 2001

(65) Prior Publication Data

US 2002/0138026 A1 Sep. 26, 2002

(51) Int. Cl.⁷ .................................................. A61F 5/00
(52) U.S. Cl. ........................ 602/21; 602/5; 602/20; 602/22; 602/23; 602/30
(58) Field of Search ............................ 602/23, 30, 60, 602/62, 63, 65; 128/882, 893, 894; 623/29, 33, 36, 53; 2/239; 36/29, 71, 72, 93, 110; 606/53, 72, 60, 62, 59, 86

(56) References Cited

U.S. PATENT DOCUMENTS

| | | | | |
|---|---|---|---|---|
| 616,810 A | * | 12/1898 | Simister | |
| 3,423,095 A | * | 1/1969 | Cox | |
| 3,643,659 A | * | 2/1972 | Storer | |
| 3,887,946 A | * | 6/1975 | Laskin | |
| 3,938,510 A | * | 2/1976 | Gerber | |
| 4,061,138 A | * | 12/1977 | Bernstein | 602/11 |
| 4,069,599 A | * | 1/1978 | Alegria | |
| 4,177,583 A | * | 12/1979 | Chapman | 36/77 R |
| 4,414,964 A | * | 11/1983 | Farino et al. | 602/30 |
| 4,454,872 A | * | 6/1984 | Brouhard | 602/11 |
| 4,729,369 A | * | 3/1988 | Cook | |
| 5,074,060 A | * | 12/1991 | Brncick et al. | 36/77 R |
| 5,113,849 A | * | 5/1992 | Kuiken | |
| 5,185,945 A | * | 2/1993 | Nielson et al. | |
| 5,430,960 A | * | 7/1995 | Richardson | 36/89 |
| 5,462,069 A | * | 10/1995 | Cohen | 128/893 |
| 5,497,789 A | * | 3/1996 | Zook | 128/894 |
| 5,499,982 A | * | 3/1996 | Adamson | 606/53 |
| 5,555,584 A | * | 9/1996 | Moore, III et al. | |
| D391,744 S | * | 3/1998 | McMaster | D2/913 |
| 5,822,888 A | * | 10/1998 | Terry | |
| D404,844 S | * | 1/1999 | Namin | D29/100 |
| 5,921,243 A | * | 7/1999 | Shakoor | |
| 5,980,475 A | * | 11/1999 | Gibbsons | 602/11 |
| 6,056,712 A | * | 5/2000 | Grim | |
| 6,409,692 B1 | * | 6/2002 | Covey | |

\* cited by examiner

Primary Examiner—Nicholas D. Lucchesi
Assistant Examiner—Lalita M. Hamilton
(74) Attorney, Agent, or Firm—Patton Boggs LLP

(57) ABSTRACT

A protective apparatus for protecting an end of an appendage from physical contact after a surgical procedure. The apparatus has a base that affixes to an appendage. An attachment assembly affixes the base to the appendage. A protective guard extends outward from the base and bends back toward the base to at least partially enclose an end of the appendage. The guard creates a buffer that encloses space between the guard and the end of the appendage to prevent the end of the appendage from contacting the guard when a force is applied to the guard.

11 Claims, 6 Drawing Sheets

POST SURGICAL APPENDAGE PROTECTOR

FIELD OF THE INVENTION

Figure 1:
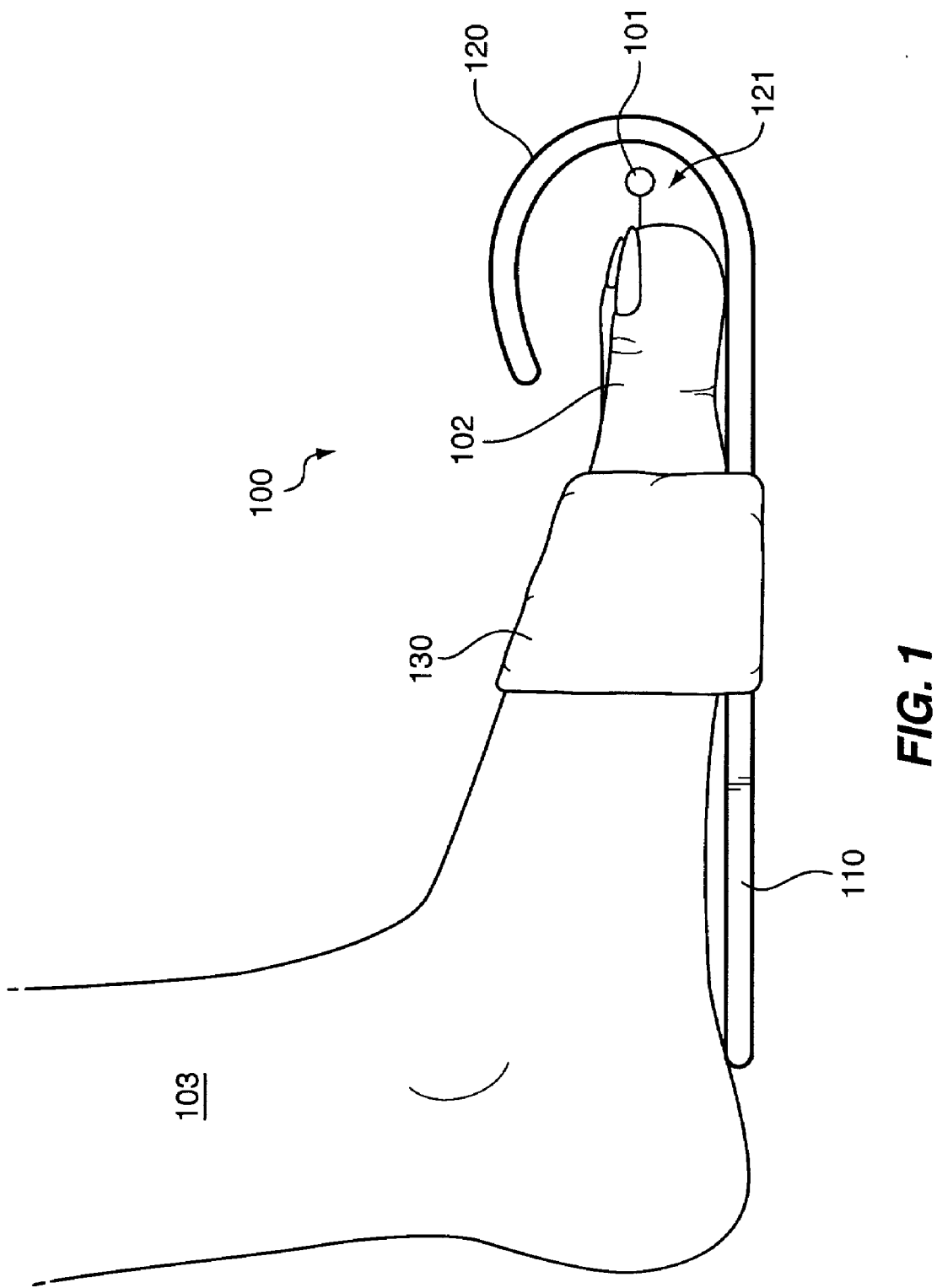

This invention relates to an apparatus that protects a tender end of an appendage or pins protruding from an appendage after a surgery. More particularly, this invention relates to a splint that is fastened to an appendage and a cover that projects out from an end of a base of the splint to cover an end of the appendage and/or a pin that projects out of the appendage. The cover prevents the end of the appendage or pins from having physical contact with other objects in order to prevent a force from being applied to the end of the appendage or pins.

1. Problem

It is also common for an end of an appendage to be extremely sensitive after a surgical procedure. Therefore, it is desirable to avoid any physical contact with the appendage. For example, a person that has a bunionectomy, such as a Mcbride osteotomy, has a bunion removed from a toe or foot area. This toe or foot area is extremely sensitive and the person experiences extreme pain from any physical contact with the area.

In many other surgical procedures, it is common to insert a surgical pin that remains in place after a procedure. The surgical pin holds bones and/or tissue in place to induce healing of a fracture or other malady in a proper position. For example, it is common in serious fractures of a toe or foot bone to insert a pin to properly align the fractured pieces of the bone and induce proper healing. An end of the pin often protrudes from an end of a toe. The pin is very sensitive and any movement of the pin can be very painful to a patient. For this reason, there is a need for an apparatus that shields the pins from contact with outside forces.

2. Solution

The above and other problems are solved and an advance in the art is made by the appendage protector of this invention. A first advantage of this invention is that the appendage protector prevents the end of the appendage and/or pins protruding from appendages from having physical contact with other objects. This prevents a force from being applied to the end of the appendage and/or pin which may cause pain to the patient. A second advantage of this invention is that the appendage protector is removable to allow inspection of the appendage and the pin protruding from the appendage. A third advantage of this invention is that if the appendage doe not have to be inspected, the appendage protector may be incorporated into a cast or other more permanent setting. A fourth advantage of this invention is that the patient may way this protector with normal clothing. A fifth advantage of this invention is that the protector may be worn in bed to prevent undo contact of the appendage and/or pin with bedding.

In accordance with this invention, an appendage protector is formed in the following manner. The appendage protector has a base that affixes to an appendage. An attachment assembly affixes the base to the appendage. A protective guard extends outward from the base and bends back towards the base to at least partially enclose an end of an appendage and/or a pin extending from the appendage. A buffer is created by an enclosed space between the guard and the pin to prevent the pin from contacting the guard when a force is applied to the guard.

In one embodiment of this invention, the attachment assembly is formed in the following manner. The base of the protector has slots on opposing sides. A strap fits through the slots to and is tightened around the appendage to affix base to the appendage. The strap may include opposing velcro strips to secure the base to the appendage.

In an alternative embodiment, the attachment assembly may be a bandage that wraps around the base and the appendage to affix the base to the appendage.

In another alternative embodiment, the attachment assembly is a cast that incorporates the base and surrounds the appendage.

In one embodiment, the base may include contoured indentures in a surface of the base contacting the appendage that hold the appendage in place. If the appendage is a foot, the contoured indentures may include an arch support. If the appendage is a foot, the contoured indentures may also include a heel cup. If the appendage is a finger, the contoured indentures may include an imprint of a palm.

If the appendage is a foot or a toe, a heel may be affixed to a bottom side of the base to facilitate walking.

BRIEF DESCRIPTIONS OF THE DRAWINGS

Figure 2:
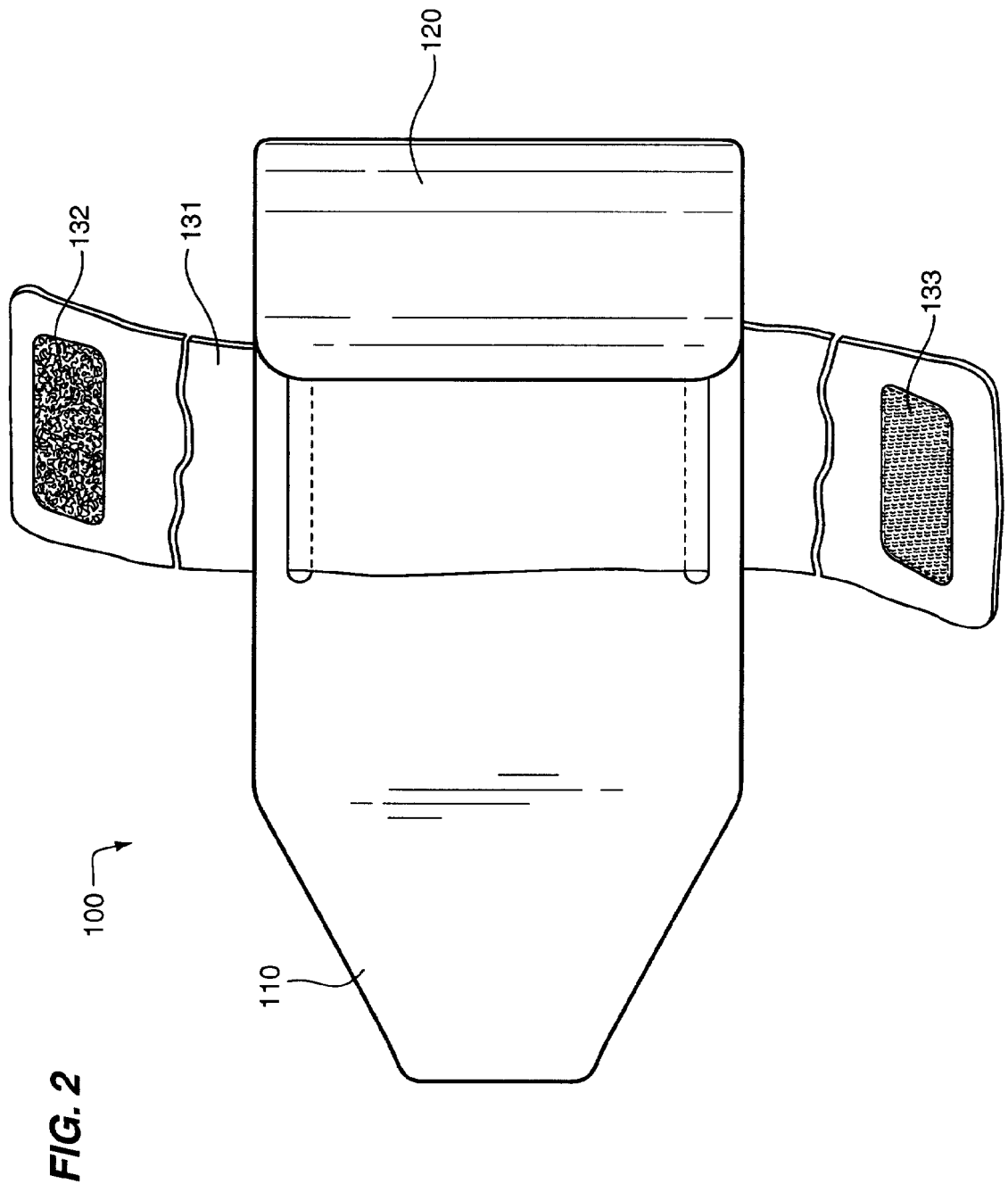
Figure 3:
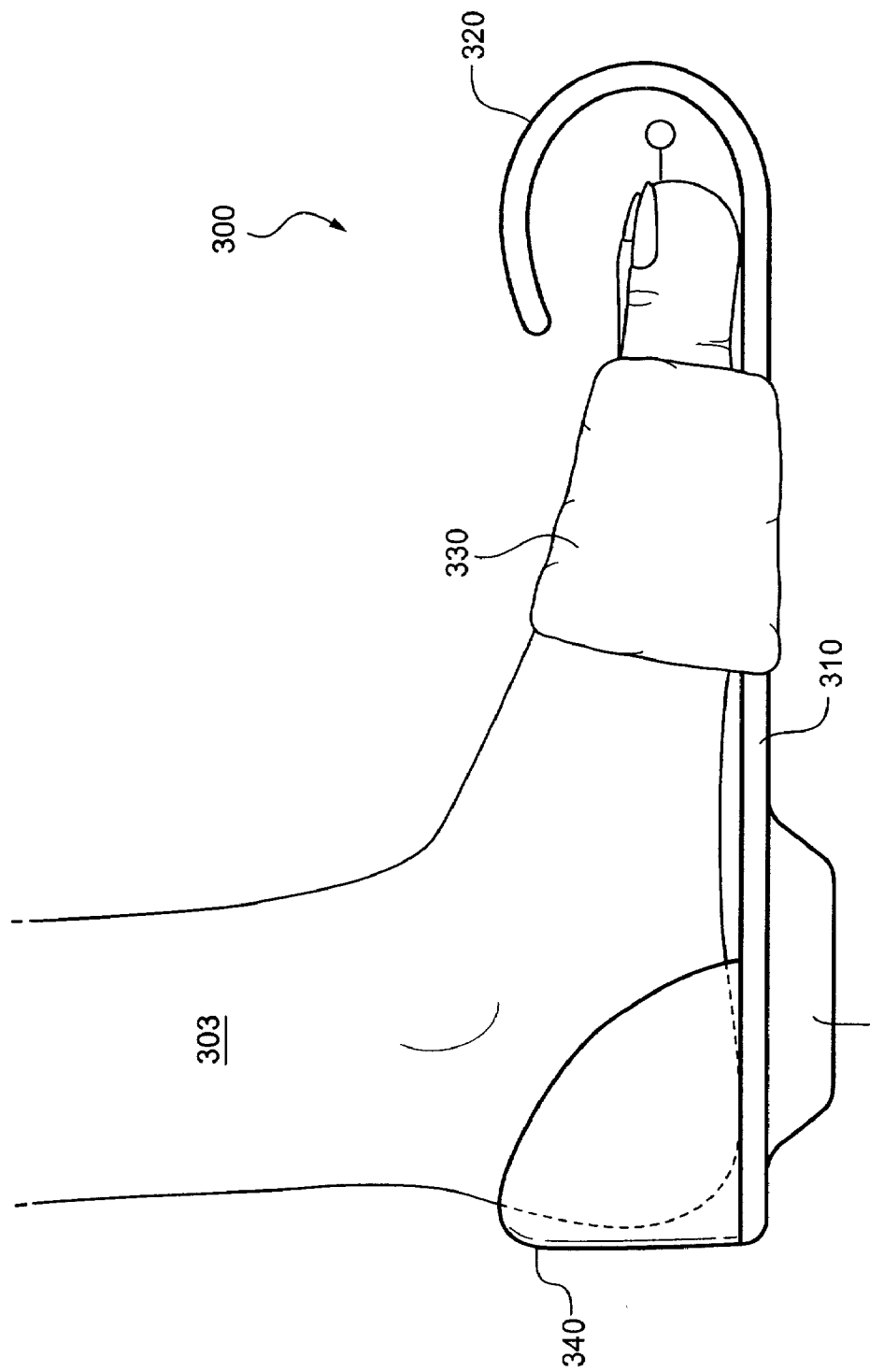
Figure 4:
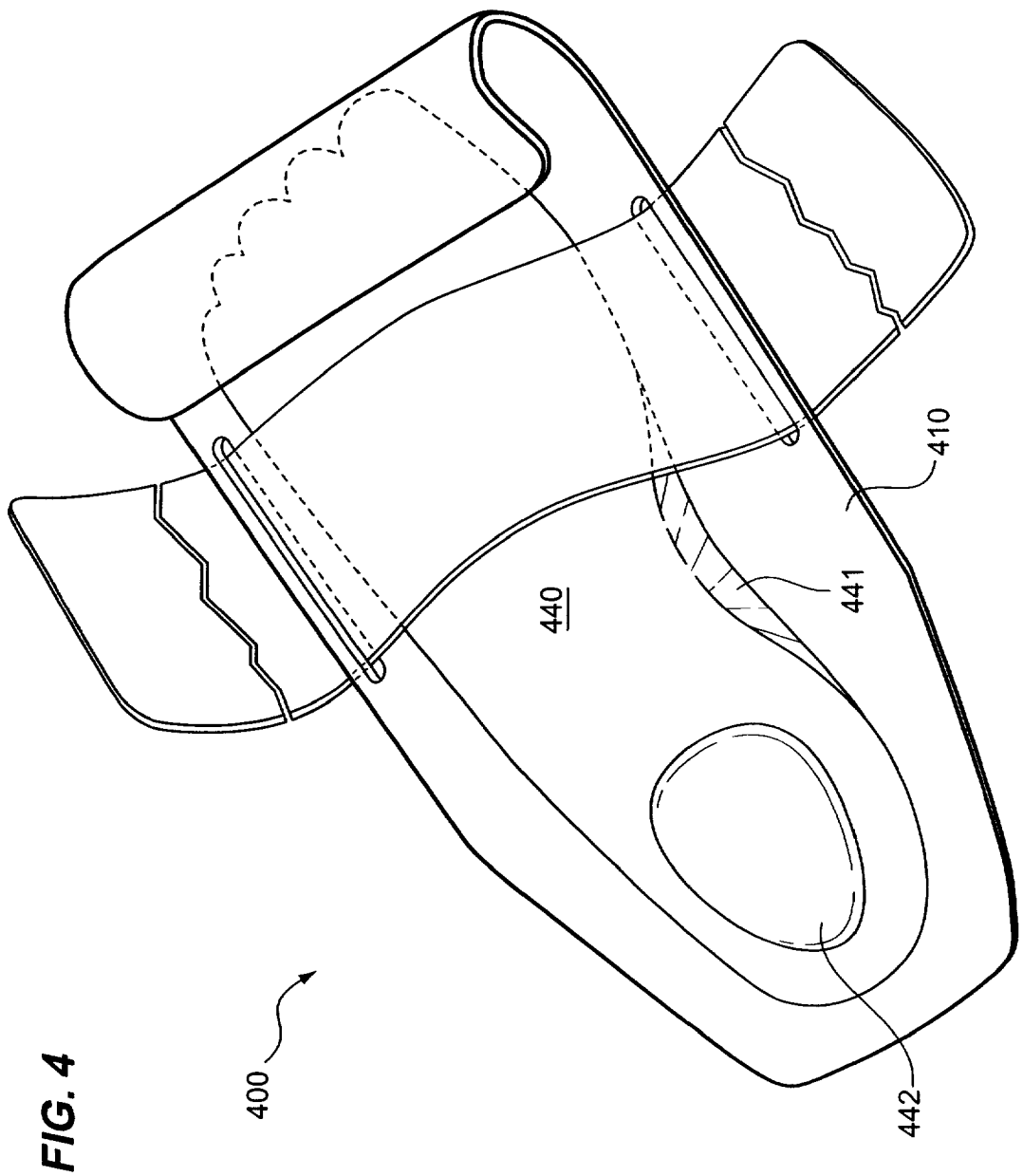
Figure 5:
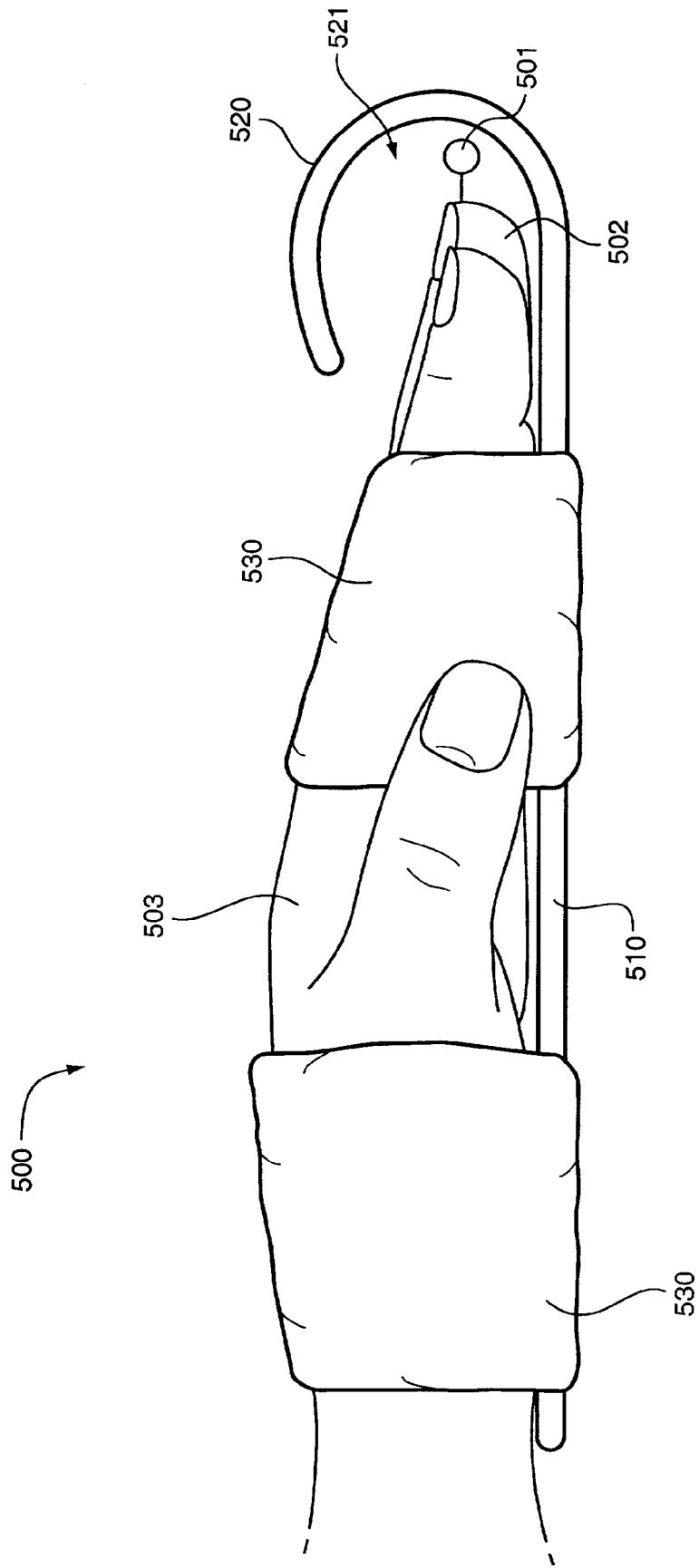

The above and other features of this invention are set forth in the detailed description below and the following drawings:

FIG. 1 illustrating a first embodiment of this invention protecting a pin protruding from a toe;

FIG. 2 illustrating a second embodiment of this invention protecting a pin protruding from a finger;

FIG. 3 illustrating the first embodiment of this invention from a top side view;

FIG. 4 illustrating a preferred second embodiment of this invention;

FIG. 5 illustrating a preferred first embodiment of this invention; and

Figure 6:
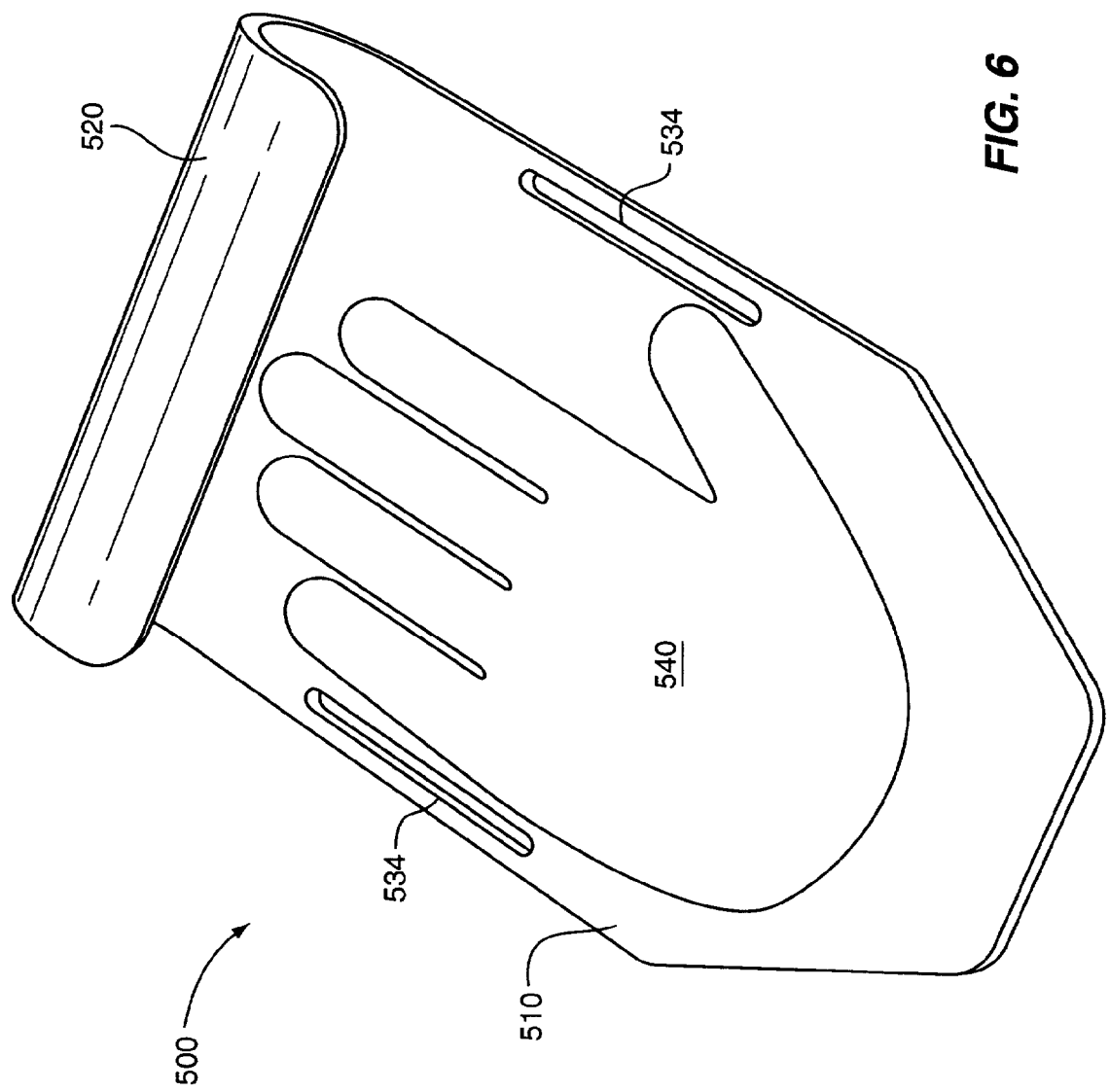

FIG. 6 illustrating a preferred second embodiment of this invention.

DETAILED DESCRIPTION

This invention is an apparatus that protects an end of an appendage and/or a pin that protrudes from an appendage to prevent injury to a patient from inadvertent contact between the end of the appendage and/or the pin with other objects. The present invention may be used alone or incorporated into a cast or other device to protect the end of the appendage and/or pins.

FIG. 1 illustrates a toboggan-shaped post surgical appendage protector 100 in a first embodiment of this invention. In FIG. 1 a toe 102 has a pin 101 protruding out of an end of the toe 102. Protector 100 includes base 110 which includes a rigid substantially elongated flat portion, a curved portion creating protective guard 120, and attachment assembly 130. Base 110 is a long, flat surface that supports the appendage. Base 110 affixes to an appendage, such as foot 103 to secure to the protective guard over a pin 101. One skilled in the art will recognize that although a foot 103 and toe 102 are shown in FIG. 1, this invention may be used with any number of appendages as shown below. For purposes of this discussion, appendage refers to any extremity that may have a pin inserted to align tissue or may be extremely sensitive after a surgical procedure.

Attachment assembly 130 affixes base 110 to foot 103 and secures base 110 in place. Attachment assembly 130 may include a strap affixed to base 103. Attachment assembly 130 may also simply be a bandage or other type of wrapping that is wrapped around foot 102 and base 110 to secure base 103 in place.

The curved portion of the toboggan-shaped member creating protective guard 120 extends outward from base 110 and bends back towards base 110 [to at least partially enclose] without touching and enclosing toe 102 and/or a pin extending from toe 102 as illustrated in FIG. 1. One skilled in the art will recognize that protective guard 120 may also have sides that totally enclose toe 102 and/or pin 101 without altering the function of protective guard 120. Protective guard 120 provides a buffer 121 created by [enclosed] space between protective guard 120, toe 102, and pin 101. The curved portion creating protective guard 120 is adapted to be distal from toe 102 to separate protective guard 120 from toe 102 to accommodate surgical pin 101 protruding from toe 102. Thus preventing the end of toe 102 and/or pin 101 from contacting the inside of protective guard 120 when a force is applied to protective guard 120.

FIG. 2 illustrates protector 100 from a top side and without a foot 103 inserted into the protector 100. This further shows attachment assembly 130. Attachment assembly 130 includes slots 134 on opposing sides of base 110. Slots 134 are longitudinal slots that run along side of foot 103 or other appendage (Not shown in FIG. 2). Strap 131 is inserted through slots 134 and is fastened to secure the base 110 to foot 103. Strap 131 may include opposing velcro strips 132 and 133 to fasten the strap. Alternatively, buckles and holes may be used or any other fastening system one skilled in the art may desire.

FIG. 3 illustrates a protector 300 that is a preferred embodiment of the first embodiment. Protector 300 includes base 310, attachment assembly 330, and protective guard 320. In addition, protector 300 includes heel 350 and heel cup 340. Heel 350 is affixed to a bottom side of base 310. Heel 350 facilitates walking by giving an impact point for a foot. Heel cup 340 is a wall made of plastic or cloth formed in a semi-circle around an end of base 310 opposite protective guard 320. Heel cup 340 receives a heel of foot 303 and sets the heel in place to facilitate walking.

FIG. 4 illustrates another alternative first embodiment. Protector 400 includes contoured indentures 440 in a surface of base 410 contacting the appendage to hold the appendage in place. In this embodiment, contoured indentures 440 are formed in the shape of a foot. Contoured indentures may include an arch support 441 that is positioned to contact the arch in a curved manner and that is elevated compared to the rest of the base to provide support to an arch. Likewise, heel 442 may be recessed to receive a heel of the foot and keep the heel in place. A second alternative to the first embodiment is to insert protector 100 (Shown in FIGS. 1 and 2) into an orthopedic shoe.

FIG. 5 illustrates a second embodiment of this invention in which protector 500 protects a pin 501 protruding from a finger 502 of hand 503. Protector 500 includes base 510, protective guard 520, and attachment assembly 530. Base 510 is a long, flat surface that supports the appendage. Base 510 affixes to hand 503 to secure to the protective guard 520 over a pin 501.

Attachment assembly 530 affixes base 510 to hand 503 and secures hand 503 in place. Attachment assembly 530 may include a strap affixed to base 503. Attachment assembly 530 may also simply be a bandage or other type of wrapping that is wrapped around hand 503 and base 510 to secure base 510 in place.

Protective guard 520 extends outward from base 510 and bends back towards base 510 to at least partially enclose an end of finger 502 and a 501 pin extending from finger 502. One skilled in the art will recognize that protective guard 520 may also have sides that totally enclose finger 502 and pin 501 without altering the function of protective guard 520. Protective guard 520 provides a buffer 521 created by enclosed space between protective guard 520 and pin 501. Buffer 521 prevents an end of finger 502 and/or pin 501 from contacting the inside of protective guard 520 when a force is applied to protective guard 520.

FIG. 6 illustrates a preferred embodiment of protector 500 from a top side and without hand 503 inserted into the protector 500. This further shows attachment assembly 530 without a strap inserted into slots 534 to provide a view of contoured indentures 540. Attachment assembly 530 includes slots 534 on opposing sides of base 510. Slots 534 are longitudinal slots that run along side of hand 502 (Not shown in FIG. 6). A strap (Not shown) is inserted through slots 534 and is fastened to secure the base 510 to hand 502. The strap may include opposing velcro strips to fasten the strap. Alternatively, buckles and holes may be used or any other fastening system one skilled in the art may desire.

In this embodiment contoured indentures include a palm print 540 that is a recessed depression formed in the shape of a hand. A hand is then fitted into the palm print and protector 500 is affixed in place. The palm print assures adequate spacing between the protector 520 and the pin 501 to prevent contact. One skilled in the art will see that the contoured indentures may be individually molded for each hand or may be a generic palm print. This is left to those skilled in the art.

The above is a description of a protector of surgical pins in accordance with this invention. It is expected that those skilled in the art can and will design alternative protectors that infringe this invention as set forth in the claims below either literally or through the Doctrine of Equivalents.

What is claimed is:

1. An independent post surgical appendage protector for use by a patient following surgery to prevent contact between an end of a foot/hand and external objects such as bedding, furniture, pets, or persons, said appendage protector comprising:

a toboggan-shaped member comprising:
   a rigid substantially elongated flat portion that extends at least partially under said foot/hand;
   a curved portion that extends outwards and arcs back toward a top of said foot/hand without touching and enclosing said end of said foot/hand to protect said end of said foot/hand;

wherein said curved portion is adapted to separate said curved portion from said end of said foot/hand to accommodate a surgical pin protruding from said end of said foot/hand and allowing an air flow to circulate to aid in healing, said foot/hand, wherein said curved portion does not enclose said foot/hand; and a means for attaching said toboggan shaped member to said foot/hand, wherein said curved portion of said toboggan shaped member is adapted to be distal from said end of said foot/hand when said toboggan shaped member is attached to said foot/hand.

2. The apparatus of claim 1 wherein sold attaching means comprises:

slots an opposing sides of said flat portion; and a strap that fits through said slots to affix said flat portion to said foot/hand.

3. The apparatus of claim 2 further comprising:

opposing Velcro strips on said strap for securing said flat portion to said foot/hand.

4. The apparatus of claim 1 wherein said attaching means comprises:

a bandage that wraps around said flat portion and said foot/hand.

5. The apparatus of claim 1 further comprising:

contoured indentures in a surface of said flat portion contacting said foot/hand that hold said foot/hand in place.

6. The apparatus of claim of claim 5 wherein said foot/hand is a foot and said contoured indentures comprise:

an arch support.

7. The apparatus of claim 5 wherein said foot/hand is a foot and said contoured indentures comprise:

a heel cup.

8. The apparatus of claim of claim 5 wherein said foot/hand is a finger and said contoured indentures comprise:

an imprint of a palm.

9. The apparatus of claim of claim 5 wherein said foot/hand is a foot and said post surgical appendage protector further comprises:

a heel on a surface of a flat portion opposite said foot/hand to facilitate walking.

10. The apparatus of claim 1 wherein said curved portion also at least partially covers a pin extending outward from said foot/hand to prevent contact with said pin.

11. The apparatus of claim 1 wherein said post surgical appendage protector is inserted into an orthopedic shoe.

* * * * *